(12) United States Patent
Luria

(10) Patent No.: US 7,087,382 B1
(45) Date of Patent: Aug. 8, 2006

(54) METHODS FOR DETECTING POLYPEPTIDES REGULATING SIGNAL TRANSDUCTION PATHWAYS

(75) Inventor: Sylvie Luria, Nes-Ziona (IL)

(73) Assignee: Stil Biotechnologies Ltd., Ramat-Gan (IL)

( * ) Notice: Subject to any disclaimer, the term of this patent is extended or adjusted under 35 U.S.C. 154(b) by 449 days.

(21) Appl. No.: 10/130,137

(22) PCT Filed: Oct. 25, 2000

(86) PCT No.: PCT/IL00/00680

§ 371 (c)(1),
(2), (4) Date: May 16, 2002

(87) PCT Pub. No.: WO01/38569

PCT Pub. Date: May 31, 2001

Related U.S. Application Data

(63) Continuation-in-part of application No. 09/449,532, filed on Nov. 29, 1999, now abandoned.

(51) Int. Cl.
*C12Q 1/68* (2006.01)
*C12N 15/00* (2006.01)

(52) U.S. Cl. .................................... 435/6; 435/320.1
(58) Field of Classification Search .................. 435/6, 435/69.1, 235.1, 320.1, 455, 471, 325, 252.3, 435/69.7; 536/23.1, 24.1
See application file for complete search history.

(56) References Cited

U.S. PATENT DOCUMENTS

| 5,482,835 A | 1/1996 | King et al. |
| 5,753,446 A | 5/1998 | Johnson |
| 5,876,972 A | 3/1999 | Spengler et al. |

*Primary Examiner*—James Ketter
*Assistant Examiner*—Konstantina Katcheves

(57) ABSTRACT

A method of detecting a polypeptide capable of regulating a transduction pathway and an expression library for use with such method are provided. The method is effected by introducing into cells endogenously expressing a trans acting regulator of the transduction pathway the expression library which includes a plurality of expression constructs each encoding a polypeptide and a reporter molecule expressible in the presence of a trans acting regulator of the transduction pathway. A level of expression within a predetermined range of the reporter is indicative of regulation of the transduction pathway by the polypeptide.

39 Claims, 9 Drawing Sheets

SEQUENCE LISTING

<160> NUMBER OF SEQ ID NOS: 16

<210> SEQ ID NO 1
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 1
ctgtgccctc actcccctgg atccctggg                                      29

<210> SEQ ID NO 2
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 2
ggtttcggag ggcccgaccg gggccggcgc                    30

<210> SEQ ID NO 3
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 3
gggctgaagc cctggactca gtacgc                        26

<210> SEQ ID NO 4
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 4
gatccactga ggtacaggag gcttgtg                       27

<210> SEQ ID NO 5
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 5
ctctgctaag ctttggtggt ggcggtgg                      28

<210> SEQ ID NO 6
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 6
ggatgcatcg taccatctac tgatgag                       27

<210> SEQ ID NO 7
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 7
gtctcggggt ggcaatggcc accgctgc                      28

<210> SEQ ID NO 8
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 8
gagcgggtgg gcacgaaggc ggagtg                                26

<210> SEQ ID NO 9
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 9
gacacggtgg tgggcacatc agctcac                               27

<210> SEQ ID NO 10
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 10
gcagcagccc ttgctgcacc ctccagagcc                            30

<210> SEQ ID NO 11
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 11
ctctgggagc tggctggagc tgggatggac                            30

<210> SEQ ID NO 12
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 12
ggtggagctg ctctcaccgc tgcccag                               27

<210> SEQ ID NO 13
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 13
cggtaggcgt gtacggtggg aggtc                                 25

<210> SEQ ID NO 14
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 14
ctctccactg acagagaact tgtggccg                              28

<210> SEQ ID NO 15

-continued

```
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 15
cagctgctgg gattacacat ggcatg                                          26

<210> SEQ ID NO 16
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 16
gtcgaggctg atcagcgagc tctagc                                          26
```

METHODS FOR DETECTING POLYPEPTIDES REGULATING SIGNAL TRANSDUCTION PATHWAYS

This application is a CIP of Ser. No. 09/449,532, filed Nov. 29, 1999, now abandoned.

FIELD AND BACKGROUND OF THE INVENTION

The present invention relates to expression systems and methods for detecting protein—protein interactions in cells by expressing in the cells small peptide molecules and monitoring their affect on cellular signal transduction pathways. As such, the present invention enables the identification and selection of small molecules which can be used for the production of new pharmaceutical lead compounds, which can, in turn, be used for drug development and for diagnostics and research studies. The expression systems and methods of the present invention can also be used to identify novel constituents of intra cellular transduction pathways is which can be the subject of further research and study.

Control of a variety of cellular processes, including, but not limited to, growth, differentiation and function, rely upon protein—protein interactions. Protein—protein interactions are intrinsic to virtually every cellular process, such interactions control, for example, cell division processes, protein expression in cells, etc.

A signal transduction cascade is a process involving the conversion of a cell's interaction with an external regulators, such as hormones, cytokines and the like, to a specific internal response, such as upregulation or down regulation of the expression of a specific gene or genes.

A signal transduction cascade initiates at the outer surface of the cell membrane, there, an external stimulus which can be molecular (e.g., a polypeptide), or physical (e.g., light, shear stress, etc.), initiates an intra-cellular cascade of protein—protein interaction(s) and/or enzymatic reactions. This cascade ultimately leads to the upregulation or down regulation of the expression of specific gene or genes within the cell, which expression characterizes the cellular response to the external stimulus.

Signal transduction pathways are effected by protein complexes which are formed in different compartments of the cell according to the targeted signals of the proteins (Pawson T. and Scott J D., Science 1999, 278:2075–2079). Signal transduction pathways are tightly regulated processes, and many disorders and diseases are characterized in dysfunctional cellular transduction pathways.

For example, many cancer cells are characterized by dysfunctional signal transduction pathway components, which pathways regulate for example, cell proliferation.

Thus, it is of great interest to develop methods which can be used to identify polypeptides which interfere with cellular process, and as such, to control, alleviate or treat such disorders and diseases. Such polypeptides can then be used to develop novel drugs or to be used as drug targets or to identify new genes.

Currently, studies are being conducted in an effort to isolate inhibitors to cellular processes based upon either deciphering protein structure and function or studying the components involved in protein—protein interactions. Several methods with which protein—protein interactions can be studied are known in the art. The most common biochemical methods employed include, protein affinity chromatography, affinity blotting, co-immune-precipitation and protein cross linking. Molecular biology methods have been developed and include epitope tagging, two hybrid systems, three hybrid systems and phage display libraries. In addition, genetic methods which include the uncovering of genetic mutants have also been employed. For review see Phizicky E M and Fields S. Microbiol. Rev. 1995, 59:94–123.

Following, is a brief description of each of the various methods for studying protein—protein interactions commonly employed in the art.

Protein Tag:

The protein tag method involves the generation of a fusion (translational fusion of DNA sequences) between a peptide tag sequence and a defined protein sequence, so as to form a chimera protein. This chimera can serve as a tool to isolate proteins which interact with the defined protein, by using the tag sequence as an indicator for the presence of interaction. For example, antibodies generated against the tag peptide enable the visualization of the protein or protein complex on a blot or to affinity purify specific protein complexes via affinity columns or immuno-precipitation (Skolnik et al. Cell, 1991, 65:83–90).

Phage Display Library:

Phage particles consist of a nucleic acid molecule surrounded by a proteinaceous coat which enables the phage to interact with, and infect, host bacteria. Filamentous phages, such as M13, can express a fusion protein bearing a foreign peptide on the coat surface by infecting a bacterial host such as *E. Coli* (Smith G P, Science 1985, 228:1315–1317). DNA sequences coding for protein or peptide of interest are translationally fused to the N terminal of the gene encoding one of the phage coat proteins (e.g., V3 or V8 in M13). If the translational fusion does not interfere with the life cycle of the bacteriophage, the modified phage particle will express a chimeric coat protein which displays the foreign peptide or protein of interest. Phage particles "displaying" the foreign peptide or protein on their surface can be selected for by immune-affinity purification. Phage display libraries can be prepared by constructing a collection of phage particles each capable of displaying a different foreign peptide.

Random peptide phage display libraries have proved to be a useful tool for identifying the protein constituents of various protein—protein interaction reactions (Parmley, S. F. And G. P. Smith, 1989, Adv Exp Med Biol, 251:215–218; Scott, J. K. and G. P. Smith 1990, Science 249:386–390; Winter, J. 1994, Drug and Dev Res 33:71–89). Such libraries have also been used to define epitopes of monoclonal and polyclonal antibodies and to define the specificity of extra-cellular and cytosolic receptors (Devlin et al., 1990, Science 249:404–406; Doorbar J. and G Winter, 1994 J Mol Biol 244:361–369; Kay, B. K. 1995, Perp Drug disc 2:251–268).

Two-Hybrid System:

The two-hybrid system uses transcriptional activity as a measure of protein—protein interactions. This system takes advantage of the modular nature of many site specific transcriptional activators. Many transcriptional activators consist of a DNA binding domain and a transcriptional activation domain (Chein, C T. et al. Proc. Natl. Acad. Sci. 1991, 88:9578–9582, Fields S. and Song O K. 1989, Nature, 1989, 340:245–246, Fields S. and Sternglanz R. Trends. Genet. 10:286–292). The DNA binding domain serves to target the activator to a specific gene to be expressed, while the activation domain binds other proteins of the transcriptional machinery to thereby initiate transcription. The two domains of the transcriptional activator need not be covalently linked but simply brought into proximity to initiate transcription. The two domains of the transcriptional activator can be brought into proximity by a pair of interacting proteins. This is achieved by constructing two hybrids, a first hybrid in which the DNA binding domain of the transcriptional activator fused to a first protein, and a second hybrid in which the transcription activation domain of the transcriptional activator is fused to a second protein. These two hybrids are overexpressed in a cell containing one or more reporter genes under the control of a cis acting element that is known to bind the DNA binding domain. If the first and second proteins interact, the domains of the activator are brought into proximity and the reporter gene is activated. Since the two hybrid system involves the utilization of nucleus functioning transcriptional activator this system is limited to interactions which can occur in the nucleus, thus preventing its use with certain extracellular proteins. Numerous variations on the two hybrid method have been proposed, see for example the reverse two hybrid described in U.S. Pat. No. 5,965,368 to Vidal et al.

Three Hybrid System:

The three hybrid system can be used to analyze interactions between three distinct components. This system is typically used to detect and analyze RNA protein interactions in which the binding of bifunctional RNA to each of two hybrid proteins activates transcription of a reporter gene in-vivo. This binding relies on the physical properties of the RNA and protein and not on their natural biological activities (SenGupta D J. et al., 1996, Proc. Natl. Acad. Sci. 93:8496–8501).

Although the above described methods enable the detection and subsequent isolation of interacting proteins, these methods are generally used to detect interactions in which one component is a known component, and as such in cases where a protein which interacts with transduction pathway proteins is sought, hybrids must be constructed for all of the proteins involved in the pathway.

There is thus a widely recognized need for, and it would be highly advantageous to have, an in-situ method for detecting and isolating polypeptides which regulate transduction pathways devoid of the above limitations.

SUMMARY OF THE INVENTION

According to one aspect of the present invention there is provided an expression system useful for the detection and isolation of a polypeptide capable of regulating a transduction pathway, the expression system comprising (a) a first expression construct including a first coding region encoding a reporter molecule, the first coding region being under transcriptional control of a cis acting regulatory sequence element, the cis acting regulatory sequence element being regulatable by a trans acting regulator of the transduction pathway; and (b) an expression library including a plurality of second expression constructs, each of the plurality of second expression constructs of the expression library including a second coding region encoding for one of a plurality of polypeptides, the second coding region being under a transcriptional control of a promoter, such that when the first expression construct and a second expression construct of the plurality of second expression constructs of the expression library are introduced into a cell, the cell endogenously expressing the trans acting regulator of the transduction pathway, a level of expression of the reporter molecule in the cell is indicative of regulation of the transduction pathway by a specific polypeptide of the plurality of polypeptides expressed by the cell from the second expression construct.

According to another aspect of the present invention there is provided an expression system useful for the detection and isolation of a polypeptide capable of regulating a transduction pathway, the expression system comprising (a) a first expression construct including a first coding region encoding a transactivator, the first coding region being under transcriptional control of a cis acting regulatory sequence element, the cis acting regulatory sequence element being regulatable by a trans acting regulator of the transduction pathway; and (b) an expression library including a plurality of second expression constructs, each of the plurality of second expression constructs of the expression library including a second coding region encoding for one of a plurality of polypeptides, each of the plurality of second expression constructs of the expression library further including a third coding region encoding a reporter molecule, the second coding region and the third coding region being under a transcriptional control of at least one promoter being regulatable by the transactivator, such that when the first expression construct and a second expression construct of the plurality of second expression constructs of the expression library are introduced into a cell, the cell endogenously expressing the trans acting regulator of the transduction pathway, a level of expression of the reporter molecule in the cell is indicative of regulation of the transduction pathway by a specific polypeptide of the plurality of polypeptides expressed by the cell from the second expression construct.

According to yet another aspect of the present invention there is provided an expression library useful for the detection and isolation of a polypeptide capable of regulating a transduction pathway, the expression library comprising a plurality of expression constructs each including a first coding region encoding one polypeptide of a plurality of polypeptides and a second coding region encoding a reporter molecule, the first and the second coding regions being under the transcriptional is control of at least one cis acting regulatory sequence element being regulatable by a trans acting regulator of the transduction pathway, such that when an expression construct of the plurality of expression constructs of the expression library is introduced into a cell, the cell endogenously expressing the trans acting regulator of the transduction pathway, a level of expression of the reporter molecule in the cell is indicative of regulation of the transduction pathway by a specific polypeptide of the plurality of polypeptides expressed by the cell from the second expression construct.

According to further features in preferred embodiments of the invention described below, the transactivator is selected from the group consisting of a transcriptional regulator and an RNA polymerase.

According to still further features in the described preferred embodiments the RNA polymerase is selected from the group consisting of a bacterial RNA polymerase and a bacteriophage RNA polymerase.

According to still further features in the described preferred embodiments the bacteriophage RNA polymerase is selected from the group consisting of a T7 RNA polymerase, a T3 RNA polymerase and an SP6 RNA polymerase.

According to still further features in the described preferred embodiments the reporter molecule is an enzyme.

According to still further features in the described preferred embodiments the reporter molecule is a fluorescer.

According to still further features in the described preferred embodiments the fluorescer is selected from the group consisting of green fluorescent protein, blue fluorescent protein, yellow fluorescent protein and cyan fluorescent protein.

According to still further features in the described preferred embodiments the reporter molecule is a eukaryotic cell surface marker.

According to still further features in the described preferred embodiments the first expression construct further includes a selectable marker sequence.

According to still further features in the described preferred embodiments the selectable marker sequence encodes a polypeptide capable of conferring antibiotic resistance to the cell. According to still further features in the described preferred embodiments the second expression construct further includes a selectable marker sequence.

According to still further features in the described preferred embodiments the selectable marker sequence encodes a polypeptide capable of conferring antibiotic resistance to the cell.

According to still further features in the described preferred embodiments the cis acting regulatory sequence element is selected from the group consisting of a promoter, a transcriptional regulatory sequence and a translational regulatory sequence.

According to still further features in the described preferred embodiments the trans acting regulator of the transduction pathway is selected from the group consisting of a transcriptional regulator and a translational regulator.

According to still further features in the described preferred embodiments each of the plurality of second expression constructs of the expression library further includes a fourth coding region encoding a known polypeptide, the fourth coding region being translationaly fused to the second coding region encoding for one of a plurality of polypeptides.

According to still further features in the described preferred embodiments the known polypeptide is capable of targeting the one of a plurality of polypeptides into a subcellular organelle.

According to still further features in the described preferred embodiments the subcellular organelle is a nucleus.

According to still further features in the described preferred embodiments the known polypeptide is capable of targeting the one of a plurality of polypeptides out of the cell.

According to still further features in the described preferred embodiments each of the plurality of polypeptides is of a specific size selected from a size range of approximately 5 amino acids to approximately 1000 amino acids.

According to still further features in the described preferred embodiments each of the plurality of polypeptides is of a specific size selected from a size range of approximately 10 amino acids to approximately 100 amino acids.

According to still further features in the described preferred embodiments the second coding region encoding for one of a plurality of polypeptides includes a polynucleotide sequence selected from the group consisting of a portion of a polynucleotide sequence represented in a genome and a polynucleotide sequence not represented in a genome.

According to still further features in the described preferred embodiments the portion of a polynucleotide sequence represented in a genome is a digest product of a genome.

According to still further features in the described preferred embodiments the portion of a polynucleotide sequence represented in a genome is a PCR product.

According to still further features in the described preferred embodiments the polypeptide is selected from the group consisting of a characterized polypeptide, a portion of a characterized polypeptide, a combinatorial polypeptide and a polypeptide chimera.

According to still further features in the described preferred embodiments the cell is a eukaryotic cell.

According to still another aspect of the present invention there is provided a method of detecting a polypeptide capable of regulating a transduction pathway, the method comprising the step of: (a) introducing into cells endogenously expressing a trans acting regulator of the transduction pathway a first expression construct, the first expression construct including a first coding region encoding a reporter molecule, the first coding region being under transcriptional control of a cis acting regulatory sequence element, the cis acting regulatory sequence element being regulatable by the trans acting regulator of the transduction pathway; and (b) introducing into at least a portion of the cells an expression library, the expression library including a plurality of second expression constructs, each of the plurality of second expression constructs of the expression library including a second coding region encoding for one of a plurality of polypeptides, the second coding region being under a transcriptional control of a promoter; (c) monitoring a level of expression of the reporter molecule in the cells, the level of expression within a predetermined range being indicative of regulation of the transduction pathway by a polypeptide of the plurality of polypeptides; and (d) isolating the second coding region from a cell of the cells in which the level of expression of the reporter molecule is within the predetermined range.

According to an additional aspect of the present invention there is provided a method of detecting a polypeptide capable of regulating a transduction pathway, the method comprising the step of: (a) introducing into cells endogenously expressing a trans acting regulator of the transduction pathway a first expression construct, the first expression construct including a first coding region encoding a transactivator, the first coding region being under transcriptional control of a cis acting regulatory sequence element, the cis acting regulatory sequence element being regulatable by the trans acting regulator of the transduction pathway; and (b) introducing into at least a portion of the cells an expression library including a plurality of second expression constructs, each of the plurality of second expression constructs of the expression library including a second coding region encoding for one of a plurality of polypeptides, each of the plurality of second expression constructs of the expression library further including a third coding region encoding a reporter molecule, the second coding region and the third coding region being under a transcriptional control of at least one promoter being regulatable by the transactivator; (c) monitoring a level of expression of the reporter molecule in the cells, the level of expression within a predetermined range being indicative of regulation of the transduction pathway by a polypeptide of the plurality of polypeptides; and (d) isolating the second coding region from a cell of the cells in which the level of expression of the reporter molecule is within the predetermined range.

According to still further features in the described preferred embodiments steps (a) and (b) are each effected via a transformation method selected from the group consisting of biolistic bombardment, direct DNA uptake, virus mediated transformation and calcium phosphate transformation.

According to still further features in the described preferred embodiments steps (a) and (b) are co-effected via a single step.

According to still further features in the described preferred embodiments the method further including a step of selecting for cells expressing the reporter molecule prior to the introducing of the expression library.

According to still further features in the described preferred embodiments the step of monitoring a level of expression of the reporter molecule in the cells is effected via an automated cell sorter.

According to still further features in the described preferred embodiments the step of isolating the second coding region is effected via a PCR reaction using oligonucleotide primers flanking the second coding region.

According to yet an additional aspect of the present invention there is provided a method of detecting a polypeptide capable of regulating a transduction pathway, the method comprising the step of: (a) introducing into cells endogenously expressing a trans acting regulator of the transduction pathway an expression library, the expression library including a plurality of expression constructs each including a first coding region encoding one polypeptide of a plurality of polypeptides and a second coding region encoding a reporter molecule, the first and the second coding regions being under the transcriptional control of at least one cis acting regulatory sequence element being regulatable by the trans acting regulator of the transduction pathway; (b) monitoring the level of expression of the reporter molecule in the cells, a level of expression within a predetermined range being indicative of regulation of the transduction pathway by a polypeptide of the plurality of polypeptides; and (c) isolating the first coding region from a cell of the cells in which the level of expression of the reporter molecule is within the predetermined range.

According to still further features in the described preferred embodiments step (a) is effected via a transformation method selected from the group consisting of biolistic bombardment, direct DNA uptake, virus mediated transformation and calcium phosphate transformation.

The present invention successfully addresses the shortcomings of the presently known configurations by providing expression systems and methods- with which polypeptides regulating a transduction pathway can be detected and isolated. In sharp contrast to prior art methods, the present invention enables the isolation of novel transduction pathway regulators without having to first isolate or characterize transduction pathway components. As such the present invention also enables the characterization of novel transduction pathway components.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
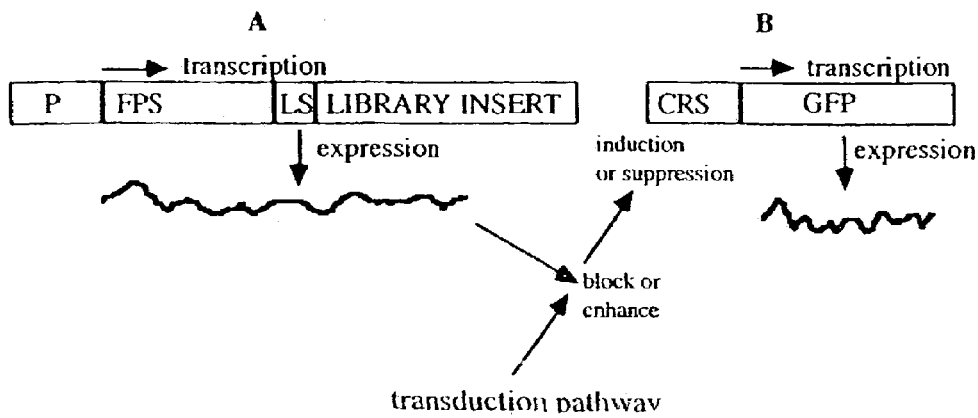

The following acronyms are presented in FIG. 14. A short definition thereof is as follows:

LS—Linker Sequence.
CRS—Cis-acting Regulatory Sequence.
GFP—Green Fluorescence Protein.
FPS—Fusion Protein Sequence.
P—Promoter Sequence.
T7—Bacteriophage T7 Promoter Sequence.
IGF—Insulin Growth Factor.
PVEGF—Promoter Vascular Endothelial Growth Factor FIG. 1 is a schematic depiction of one configuration of an expression system useful for the detection of polynucleotides encoding polypeptides regulating a transduction pathway according to the present invention.

Figure 2:
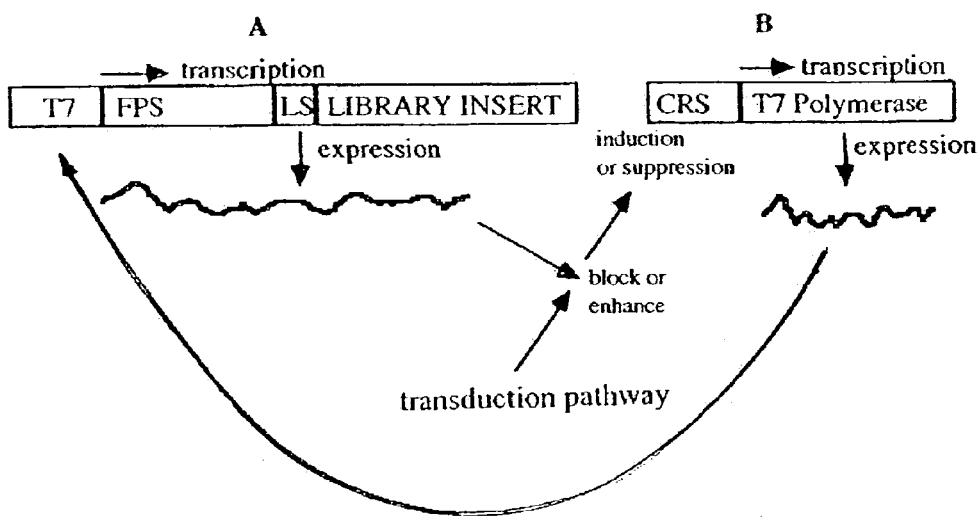

FIG. 2 is a schematic depiction of another configuration of an expression system useful for the detection of polynucleotides encoding polypeptides regulating a transduction pathway according to the present invention.

Figure 3:
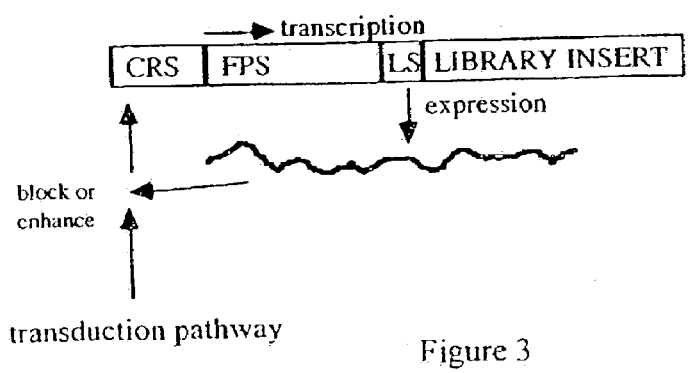

FIG. 3 is a schematic depiction of yet another configuration of an expression system useful for the detection of polynucleotides encoding polypeptides regulating a transduction pathway according to the present invention.

Figure 4:
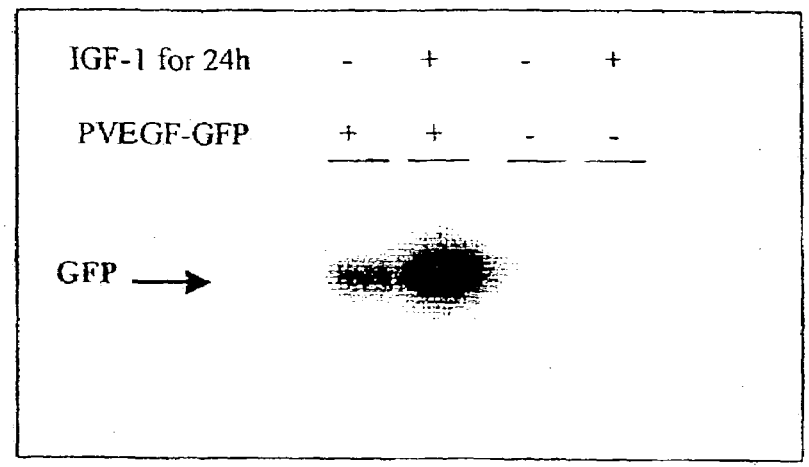

FIG. 4 is an image of a quantitative RT-PCR assay showing the quantities of GFP mRNA present in IGF treated or untreated NIH-3T3 cells that express IGF-1 receptor.

Figure 5:
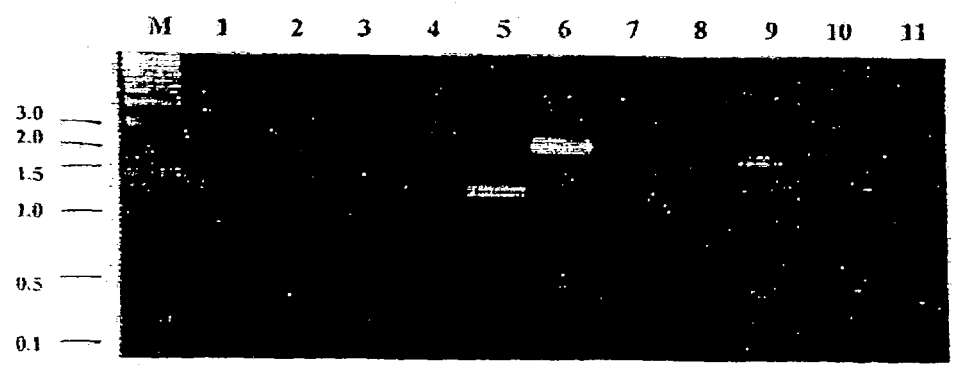

FIG. 5 is an image of the various DNA fragments utilized in the various expression libraries employed by the present invention, electrophoretically separated in an agarose gel and stained with ethidium bromide; M—molecular weight marker, lane 1—human VEGF promoter fragment, lane 2—human IGF-1 receptor amplified with primers 7 and 8, lane 3—human IRS-1 amplified with primers 5 and 19, lane 4—human IRS-1 amplified with primers 18 and 19, lane 5—human IRS-1 amplified with primers 18 and 28, lane 6—human IRS-1 amplified with primers 18 and 29, lane 7—human IRS-1 amplified with primers 24 and 27, lane 8—human IRS-1 amplified with primers 27 and 29, lane 9—EDH-1 DNA fragment, lane 10—HIV-1 NEF gene and lane 11—human CD-4 cDNA. The coordinates of the various primers are shown in FIGS. 6a–b.

Figure 6A:
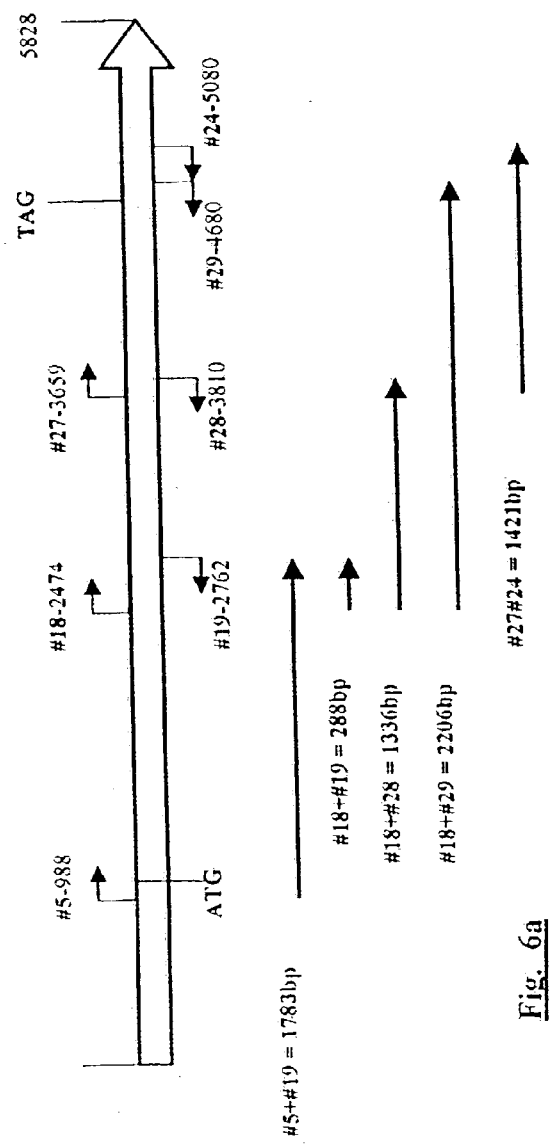
Figure 6B:
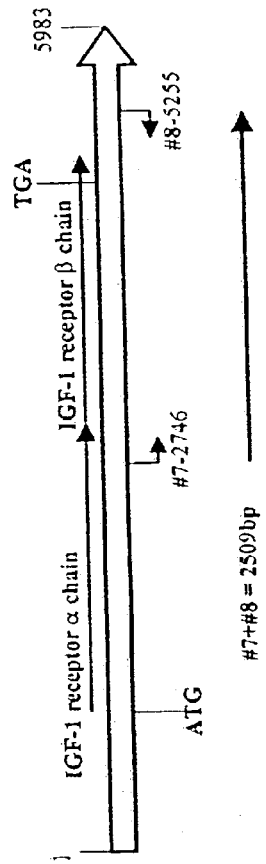

FIGS. 6a and 6b are schematic depictions representing the various DNA fragments amplified from the human IRS-1 gene (FIG. 6a) and human IGF-1 receptor gene.

Figure 7A:
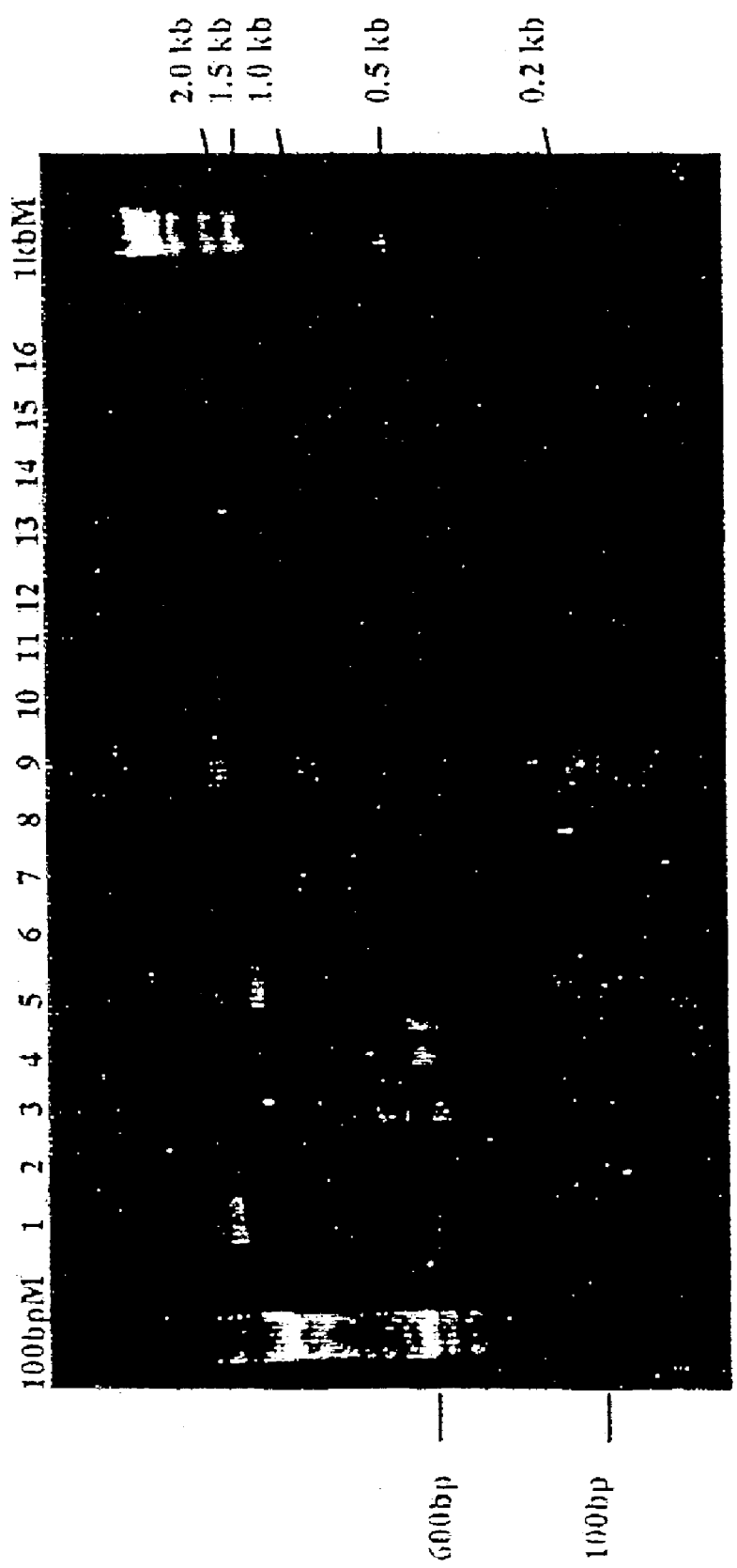
Figure 7B:
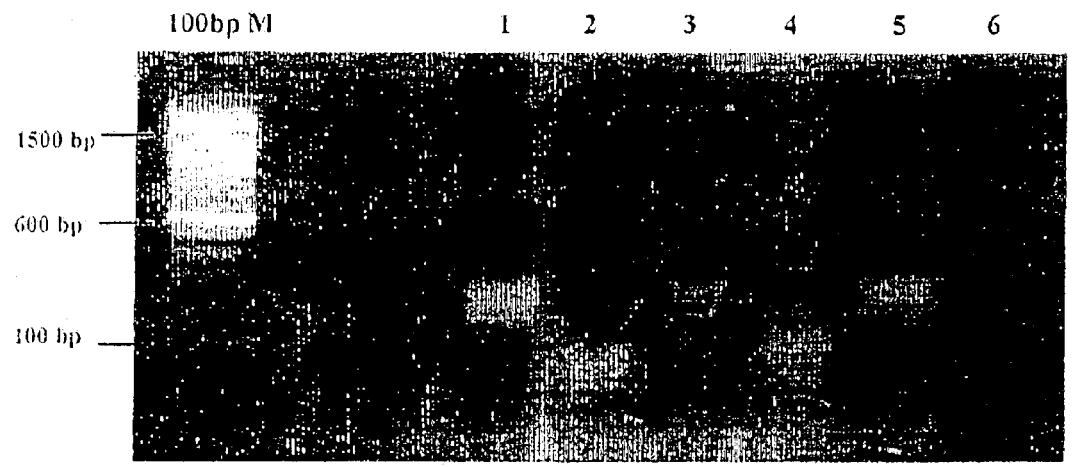

FIGS. 7a and 7b are images of agarose gels utilized for size selection of DNA fragments of IGF-1 receptor, IRS-1 and EHD-1. The DNA was digested with four cutter restriction enzymes (Bio-Labs research products) (FIG. 7a) Lanes No. 1–4 IGF-1 receptor fragments amplified with primers 7 and 8; Lanes No. 5–8 IRS-1 fragment amplified with primers 5 and 19; Lanes No. 9–12 IRS-1 fragment amplified with primers 18 and 29; Lanes No. 13–16 EHD-1 EcoR1-XhoI fragment; Lanes 1, 5, 9 and 13 undigested fragments; Lanes 2, 6, 10 and 14 HaeIII digested fragments; Lanes 3, 7, 11 and 15 AluI digested fragments; Lanes 4, 8, 12 and 16 fragments digested with BstUI and RsaI restriction enzymes. FIG. 7b shows digestion of the same fragments with DNase I; Lane 1 and 2 DNase digestion of IGF-1 receptor (7+8) fragment; Lane 3 and 4 DNase digestion of IRS-1 (5+19) fragment; Lane 5 and 6 DNase digestion of IRS—I (18+29) fragment; 100 bpM=100 base pair ladder molecular weight marker. DNA fragments of 50–300 base pairs were selected for expression libraries.

Figure 8A:
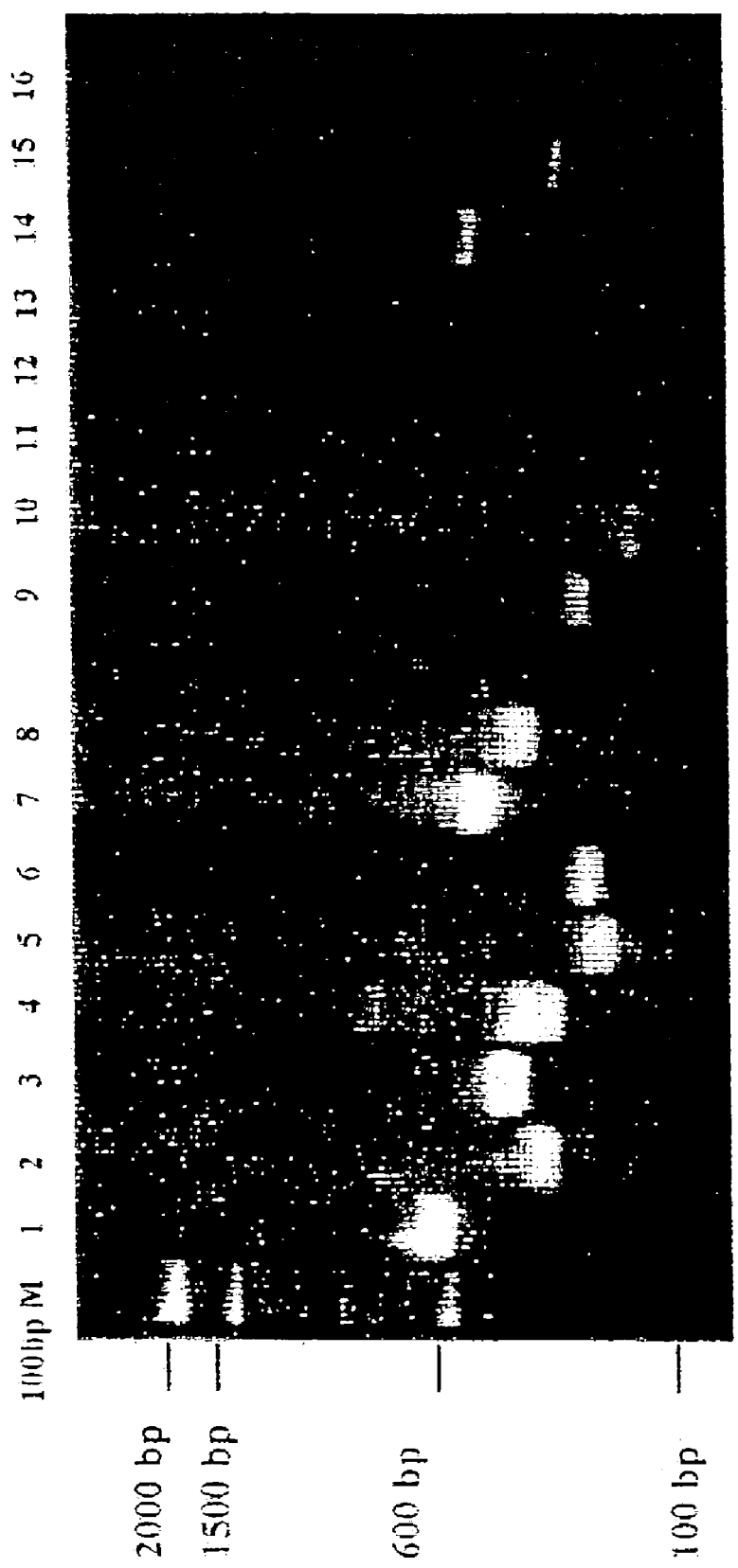
Figure 8B:
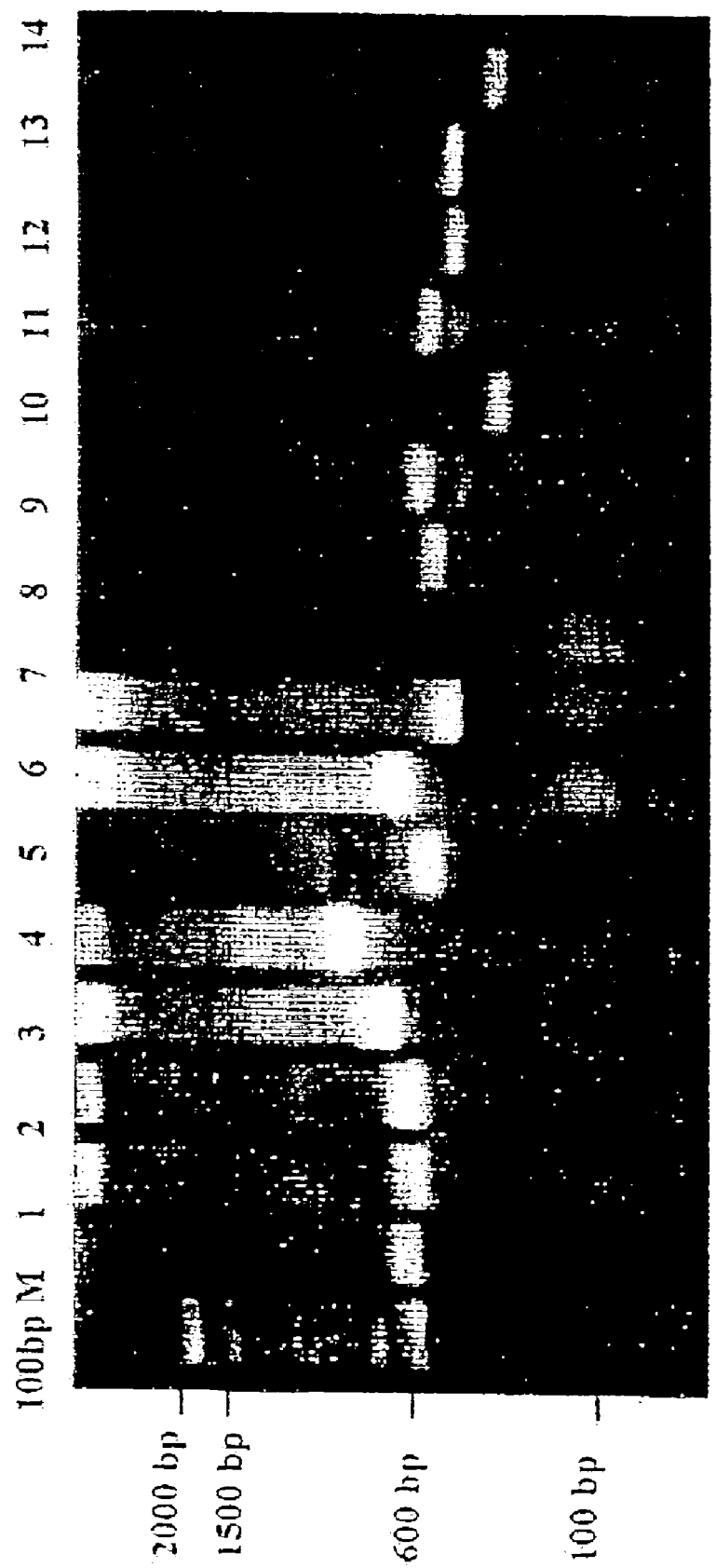
Figure 8C:
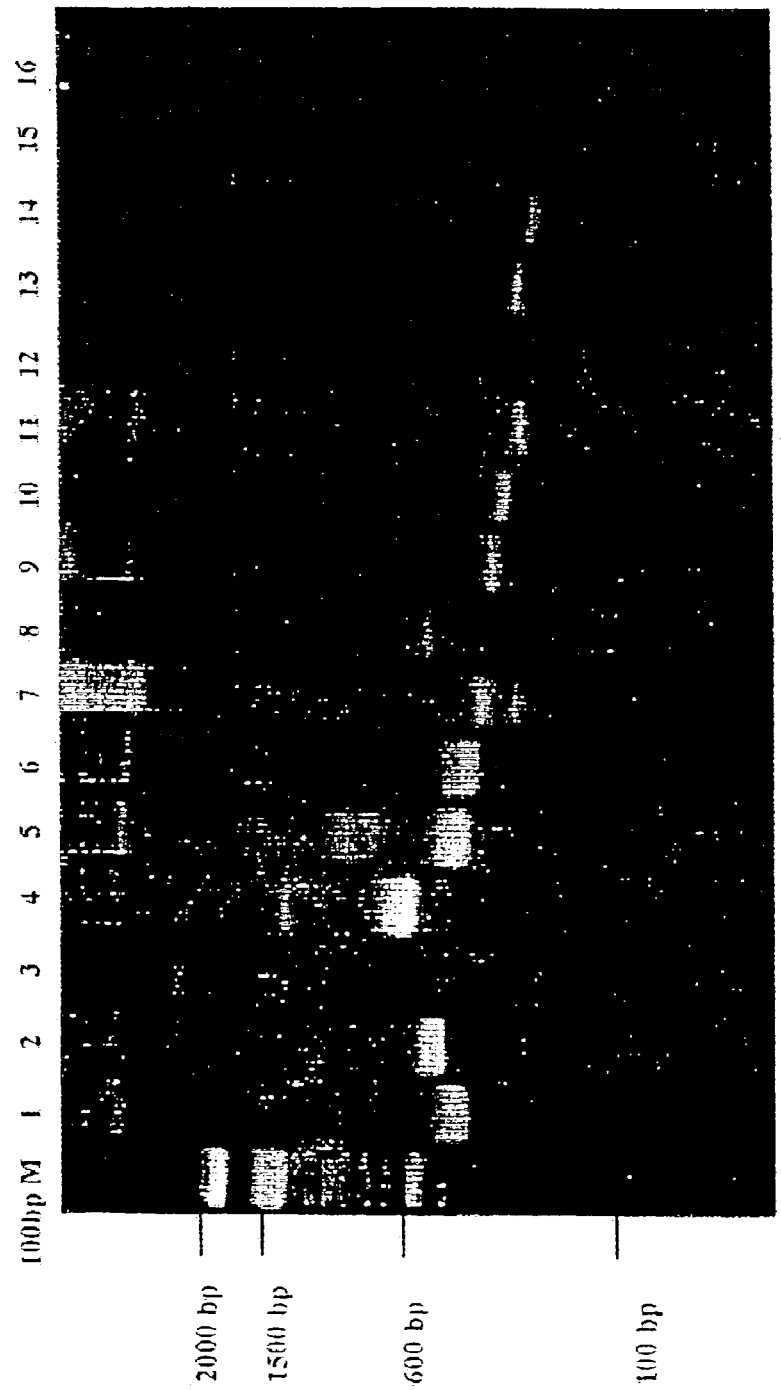
Figure 8D:
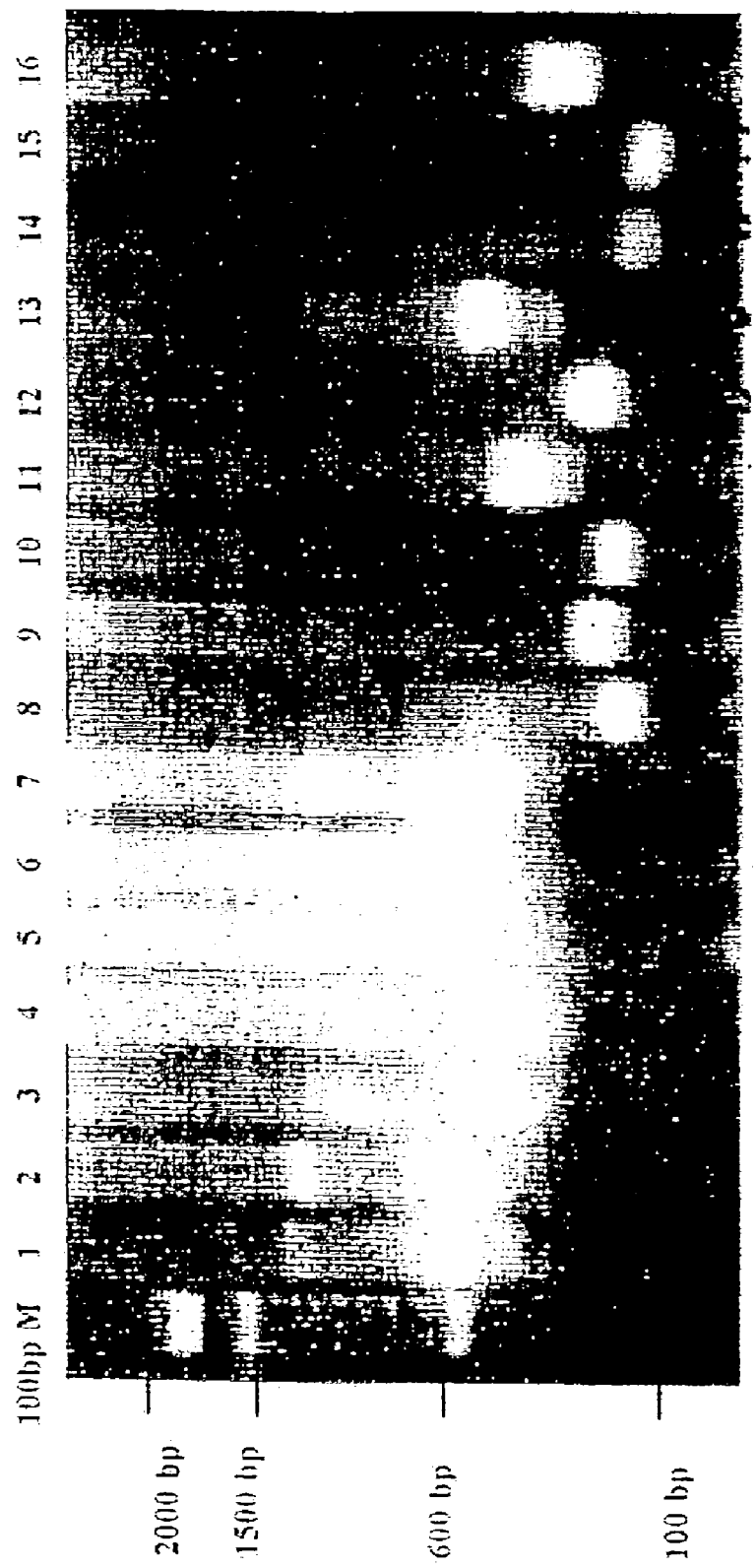

FIGS. 8a–d are images of PCR DNA analysis of individual clones from four different expression libraries; FIGS. 8a—IGF-1 receptor library clones; FIG. 8b—IRS-1 library clones 5 and 19; FIG. 8c—IRS-1 library clones 18 and 29; FIG. 8c—EHD-1 library clones; 100 bpM=100 base pair ladder molecular weight marker; 1 kbM=1 kilobase pair ladder molecular weight marker.

DESCRIPTION OF THE PREFERRED EMBODIMENTS

The present invention is of expression systems and methods which can be used to detect and isolate polypeptides capable of regulating a transduction pathway. Specifically, the present invention can be used to detect and isolate novel polypeptides or regions of known polypeptides which regulate a transduction pathway of a cell, such as, for example, a mammalian cell.

The principles and operation of the systems and methods according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Thus, according to one aspect of the present invention there is provided an expression system useful for the detection and isolation of a polypeptide capable of regulating a transduction pathway.

The expression system includes a first expression construct including a first coding region encoding a reporter molecule.

As used herein the phrase "reporter molecule" refers to a polypeptide which can be quanitated either directly or indirectly. For example a reporter molecule can be an enzyme which when in the presence of a suitable substrate generates a measurable reaction such as a color reaction. In addition a reporter can be protein which is cleaved when in the presence of a suitable protease. A reporter molecule can also be a protein which when expressed within a cell causes a developmental or morphological change in the cell, which change can be monitored.

A reporter molecule can also be a fluorescer such as, for example, the green fluorescent protein (GFP) and its derivatives. In this case, the reporter molecule can be quantified via its fluorescence which is generated upon the application of a suitable excitatory light.

Alternatively, a reporter molecule can be a polypeptide which, when expressed, is either secreted out of the cell or displayed on the cell surface. In this case the amount of the polypeptide expressed can be quantified by, for example, antibody-binding.

The first coding region is under a transcriptional control of a cis acting regulatory sequence element which is regulatable by a trans acting regulator of the transduction pathway of a cell.

As used herein the phrase "cis acting regulatory sequence element" refers to a polynucleotide sequence which binds a regulator such as the trans acting regulator of the transduction pathway of the cell and as such regulates the expression (at the transcriptional or translational level) of a coding sequence located upstream or down stream thereto. For example, a transcriptional regulatory sequence element can be a part of a promoter sequence which is activated by a specific transcriptional regulator or it can be an enhancer or suppresser sequences which can be adjacent or distant to a promoter sequence and which function in up regulating or down regulating the transcription therefrom. A cis acting regulatory sequence element can also be a translational regulatory sequence element in which case such a sequence can bind a translational regulator which up regulates or down regulates translation.

Transcriptional and translational regulators are further described hereinunder.

The phrases "transduction pathway", "signal transduction pathway" and "signal transduction cascade" are used interchangeably herein and refer to any biological pathway which is effected by components, such as, for example, trans acting regulators, which can be, for example, responsible for switching gene expression on or off or otherwise regulating the level of gene expression. A signal transduction pathway can be present in the cell at all times or alternatively and typically it is switched on in response to a stimulus. Thus, a cell endogenously expressing the trans acting regulator of the transduction pathway can be a cell in which this transduction pathway is active at all times, or alternatively and presently preferably, it is a cell in which the transduction pathway is activated via an externally applied stimulus. Still alternatively, a transduction pathway can be genetically engineered into a cell by recombinantly expressing some or all of its components in a cell.

Trans acting regulators include transcriptional activators which are necessary for activation of transcription from specific promoters (for examples see Carey et al. (1989), J. Mol. Biol., 209:423–432; Cress et al. (1991) Science, 251: 87–90; and Sadowski et al. (1988), Nature, 335:563–564).

Trans acting regulators can also be translational activators. Translational activators are exemplified by the cauliflower mosaic virus translational activator (TAV). See, for example Futterer and Hohn (1991) EMBO J. 10:3887–3896. In this system a dicistronic mRNA is produced. That is, two coding regions are transcribed in the same mRNA from the same promoter. In the absence of TAV, only the first cistron is translated by the ribosomes. However, in cells expressing TAV, both cistrons are translated.

The term "expression" refers to the biosynthesis of a gene product. For example, in the case of a structural gene, expression involves the transcription of the structural gene into messenger RNA (mRNA) and the translation of the mRNA into one or more polypeptides. The term also refers to the expression of regulatory RNA sequences, e.g., endogenous ribozymes.

The expression system according to this aspect of the present invention further includes an expression library composed of a plurality of second expression constructs. Each of the plurality of second expression constructs of the expression library includes a second coding region encoding for one of a plurality of polypeptides. The second coding region is of a polynucleotide sequence which is either derived from a genomic fragment (i.e., it typically includes both exon and intron sequences) or alternatively it can be derived from a synthetic polynucleotide sequence, such as, for example, nucleic acid amplified from mRNA, cDNA or genomic DNA. Regardless of the source of the polynucleotide sequence, the second coding region codes for a polypeptide.

As used herein the term "polypeptide" refers to an amino acid polymer of a length anywhere between a few or several amino acids to several thousand amino acids, which can represent either a fraction or an entire sequence of a characterized or uncharacterized protein from any organism. It will be appreciated that although polynucleotide fragments originating either from genomic or mRNA sources are preferably utilized to code for the polypeptides of the polypeptide library, the present invention can also be used to probe the transduction pathway regulative effect of various combinatorial polynucleotide sequences, which, for example, can be synthetic or shuffled DNA segments of different lengths. Thus, the term polypeptide is also used herein to refer to chimeras and combinatorial polypeptides encoded by polynucleotides produced by various synthesis methods which are well known in the art.

The second coding region of the second expression constructs according to this aspect of the present invention is under a transcriptional control of a promoter which is typically a constitutive promoter, although an inducible promoter or a tissue specific promoter can also be used.

According to this aspect of the present invention, when the first expression construct and a second expression construct are introduced into a cell, which cell endogenously expresses the trans acting regulator of the transduction pathway which regulates the cis acting regulatory sequence element present in the first expression construct, a level of expression of the reporter molecule in the cell is indicative of regulation of the transduction pathway by a specific polypeptide expressed from the second coding region of the second expression construct.

It will be appreciated that both the first and second expression constructs preferably also include a selectable marker such that cells expressing these constructs can be selected for. Examples to selectable markers include antibiotic resistance genes and reporters. Thus, the reporter molecule expressed from the first expression construct can also serve as a selectable marker.

It will further be appreciated that since transduction pathways typically involve extracellular components, such as cell surface receptors, and/or intra nuclear components such as transcriptional activators, the second construct preferably also includes a third coding region which is translationaly fused to the second coding region and which codes for a known polypeptide. This polypeptide can serve as either a nuclear localization signal (NLS) or as a cell secretion signal. Alternatively, this polypeptide can also serve to stabilize or solubilize the polypeptide expressed from the second coding region.

Thus, a polypeptide expressed from the second expression construct which can regulate (either suppress or enhance) the transduction pathway will effect the level of expression of the reporter molecule and as such, a cell which expresses this polypeptide can be detected and isolated based on the level of expression of the reporter molecule. It will be appreciated that in order to ascertain if the level of expression of the reporter molecule is indicative of transduction pathway regulation, the level of expression of the reporter molecule in this cell can be correlated to that in a control cell which does not express the second expression construct, or alternatively to an average reporter level present in a plurality of cells which express different polypeptides. It will be appreciated that in order to uncover polypeptides which enhance transduction pathways a cell in which the transduction pathway is not activated is preferably utilized.

Although as described hereinabove, the regulation of a transduction pathway is typically effected at the polypeptide level, it is possible that transcription products of specific second coding regions can also regulate a transduction pathway. For example, RNA sequences which regulate gene expression are known, thus transcription products of various second expression constructs can function, for example, as antisense RNA or ribozyme sequences which block the expression (e.g., transcription, RNA processing such as splicing and/or translation) of a transduction pathway constituent or constituents.

In any case, a cell in which a level of a reporter molecule falls within a predetermined range, is isolated. For example, a fluorescence activated cell sorter (FACS) can be used to automatically sort cell expressing GFP as a reporter molecule. The second coding region can then be isolated from the sorted cells by utilizing, for example, a polymerase chain reaction (PCR) and specific oligonucleotide primers which flank the second coding sequence.

The recovered second coding sequence(s) can then be further analyzed by, for example, polynucleotide sequencing or other methods which are well known in the art.

Thus, this aspect of the present invention enables the isolation of coding sequences which can regulate a transduction pathway either at the transcriptional or translational level. Further detail of this aspect of the present invention is given in FIG. 1 which is detailed in Example 1 of the Examples section.

The present invention also provides additional expression systems with which polypeptide capable of regulating a transduction pathway can be detected and isolated.

Thus, according to another aspect of the present invention there is provided another expression system useful for the detection and isolation of a polypeptide capable of regulating a transduction pathway.

The expression system according to this aspect of the present invention includes a first expression construct including a first coding region encoding a transactivator. The first coding region is under transcriptional control of a cis acting regulatory sequence element which is regulatable by a trans acting regulator of the transduction pathway.

The system according to this aspect of the present invention also includes an expression library including a plurality of second expression constructs. Each of the plurality of second expression constructs of the expression library includes a second coding region encoding for one of a plurality of polypeptides. Each such second construct further includes a third coding region encoding a reporter molecule. The second and third coding regions are under a transcriptional control of at least one promoter which is regulatable by the transactivator. Thus, the second and third coding regions can each independently be fused to independent promoter sequences, or alternatively and preferably, the second and third coding regions are under the transcriptional control of a single promoter, such that both form a part of the same RNA transcript and are translated into a single protein chimera. In any case, both the second and the third coding regions are always co-expressed from the second construct in the presence of the transactivator. Thus, the presence of the reporter molecule in a cell is indicative of the expression of the second coding region polypeptide.

According to this aspect of the present invention when the first expression construct and a second expression construct are introduced into a cell which expresses the trans acting regulator of the transduction pathway, a level of expression of the reporter molecule in the cell is indicative of regulation of the transduction pathway by a specific polypeptide of the plurality of polypeptides expressed by the cell from the second expression construct.

Thus, this expression system differs from the earlier described expression system in that the first expression construct of the present system expresses a transactivator in response to the presence of a trans acting regulator of a transduction pathway.

As used herein the term "transactivator" refers to a polypeptide capable of activating transcription from a specific promoter. Preferably, the transactivator is an RNA polymerase. The transactivator and the promoter responsive to such a transactivator are not endogenous to the cell type utilized by the system of the present invention. Thus, if the cell type utilized is a mammalian cell, then a bacterial or bacteriophage RNA polymerase such as T7, T3 or SP6 RNA polymerases and their respective promoter sequences can be utilized.

The transactivator produced then activates transcription of both the reporter and the polypeptide of the library. It will be appreciated that according to this aspect of the present invention, the expression system forms a feedback loop within the cell. If the polypeptide expressed from the second coding region inhibits the transduction pathway, then the expression of this polypeptide is reduced and vice versa. Further detail of this aspect of the present invention is given in FIG. 2 which is detailed in Example 1 of the Examples section.

According to yet another aspect of the present invention there is provided a third expression system useful for the detection and isolation of a polypeptide capable of regulating a transduction pathway.

The expression system of this aspect of the present invention includes library of a plurality of expression constructs each including a first coding region encoding one polypeptide of a plurality of polypeptides and a second coding region encoding a reporter molecule. The first and the second coding regions are under the transcriptional control of at least one cis acting regulatory sequence element which is regulatable by a trans acting regulator of the transduction pathway. The first and second coding regions can be either independently under the control cis acting regulatory sequence element, or these sequences can be under the control of a single cis acting regulatory sequence element in which case these sequences are preferably translationaly fused.

Thus according to this aspect of the present invention when an expression construct of the expression library is introduced into a cell which endogenously expresses the trans acting regulator of the transduction pathway, a level of expression of the reporter molecule in the cell is indicative of regulation of the transduction pathway by a specific polypeptide expressed from the second expression construct. As such, the expression system of this aspect of the present invention also forms a feedback loop within the cell in which it is expressed. Further detail of this aspect of the present invention is given in FIG. 3 which is detailed in Example 1 of the Examples section.

This system of the present invention presents clear advantages over the systems described hereinabove. Since this system utilizes a single expression construct, it considerably simplifies the process of obtaining transformed cells. Furthermore, selection markers are not necessary in this case since cells expressing the reporter molecule also express the polypeptide encoded by the first coding region and thus are utilizable for detection of polypeptides which regulate a transduction pathway.

It will be appreciated that since an isolated population of cells suspected of expressing polypeptides regulating a transduction pathway include a plurality of distinct library expression constructs, each expressing a distinct polypeptide, further rounds of isolation might be necessary in order to isolate individual regulative polypeptides. In such a case, isolation of the expression constructs from the isolated cell population and reintroducing these constructs into fresh cells, serves to further isolate and characterize the regulative polypeptide(s). Such a practice can be repeated several times until isolation of a single regulative polypeptide is effected. A similar approach is also applicable in cases where a single cell expresses more than a single polypeptide, yet only one of the expressed polypeptides is a regulator of the transduction pathway.

It will further be appreciated that any of the expression constructs utilized by the present invention can be introduced into cells endogenously expressing a trans acting regulator of a transduction pathway by any transformation method known in the art. For example, introduction of polynucleotide sequences such as the expression constructs of the present invention can be facilitated by biolistic bombardment, viral infection, liposome mediated transfection, electroporation, cell fusion, direct DNA uptake and chemically mediated transformation methods utilizing, for example, calcium phosphate, polyethylene glycol and the like.

Thus the present invention provides expression systems which are useful in detecting and isolating polypeptides or active RNA molecules which regulate a transduction pathway.

While reducing the present invention to practice several reporter cell lines each containing a reporter gene were generated. These cell lines produce a readily measurable phenotype upon interaction of exogenous expressible polypeptide or polypeptide fragments with endogenous protein components which participate in intra cellular signaling transduction pathways. Further detail of these results is given in Examples 2–6 of the Examples section.

Since transduction pathways are responsible directly or indirectly for cell growth, differentiation, cellular response and the like, coding sequences which exhibit possible transduction pathway regulation can be used as possible drug candidates. Such drug candidates can be used to develop drugs useful in controlling cellular growth and differentiation and or cellular response and as such be useful in treating human tumors, cancers and other syndromes and diseases characterized by impaired signaling.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley and Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Current Protocols in Immunology" Volumes 1–111 Coligan J. E., ed. (1994); Stites et al. (eds), "Basic and Clinical Immunology" (8th Edition), Appleton and Lange, Norwalk, Conn. (1994); Mishell and Shiigi (eds), "Selected Methods in Cellular Immunology", W.H. Freeman and Co., New York (1980); available immunoassays are extensively described in the patent and scientific literature; see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization –A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Cellular signal transduction is generally initiated with the interaction of a cell surface receptor with an extracellular factor, which can be a physical factor (e.g., light or mechanical stress) or a biochemical factor (e.g., hormones, adhesion molecules, neurotransmitters, cytokines, antibodies and the like). This interaction initiates a signal that is transduced into the inner surface of the cell membrane thereby causing the intracellular domain(s) of the receptor molecule to interact with intracellular protein components. The initial intracellular receptor-target protein interactions initiate a cascade of protein interactions which propagate the signal throughout the cell along multiple intracellular pathways. These pathways culminate in the regulation of gene expression of specific genes and as such generate a specific cellular response.

Thus, specific signal transduction pathways generate specific patterns of gene regulation. Therefore, for each signaling pathway, a specific reporter cell line can be generated, which cell line would enable to monitor a given cellular signaling event by monitoring the activation or deactivation of a reporter gene encoding a reporter molecule.

As is further detailed hereinbelow, in context to specific examples of the present invention, quantitation of the reporter gene activity enables the identification of inducers or inhibitors of various cellular signaling pathways.

Example 1

Constructs

Three expression construct strategies can be utilized in order to detect polypeptides which regulate cellular signaling pathways.

FIG. 1 demonstrates a first alternative configuration of an expression system according to the present invention, which system utilizes two unique expression constructs which are introduced into a single cell.

The first expression construct (marked "A") includes a library of inserts each containing a specific expressible DNA fragment which is typically 50–300 base pairs long (marked "insert"). Each fragment is resultant from a nuclease digestion or from a PCR amplification of a particular DNA source and is translationaly fused to either the N-terminal or C-terminal portion of a known coding sequence (marked FPS in FIG. 1) which can be, for example, a targeting signal or a fusion protein which serves to solubilized the insert within the cell cytosol. This expression construct also includes a constitutive or a cell specific inducible promoter sequence (marked "P") such that when introduced into cells a fusion protein is expressed therefrom.

This expression system also includes a second expression construct (marked "B") which includes a reporter gene placed under the transcriptional control of a cis-acting regulatory sequence (marked "CRS") which is specifically regulated by constituents of a transduction pathway which can include but are not limited to trans acting regulatory elements.

FIG. 2 demonstrates a second alternative configuration of an expression system according to the present invention, which system utilizes two unique expression constructs which are introduced into a single cell. In this case the first expression construct (marked "A") includes the library inserts translationaly fused to either the N-terminal or C-terminal of a reporter gene such as for example GFP, preferably fusion is mediated by an expressible linker sequence (marked "LS") which allows both the insert and GFP to retain function following expression.

The first expression construct of this system also includes promoter sequence which is not naturally active in the cell types to be transformed with this construct, for example a bacteriophage T7 promoter sequence (marked "T7"). Thus, in the absence of a T7 polymerase, transcription cannot be initiated from this promoter.

Alternatively, the insert and GFP gene can be under the transcriptional control of a pair of identical T7 promoters. In any case, when the insert is expressed so is GFP, either as a separate protein or fused to the insert expressed polypeptide.

The system according to this aspect of the present invention also includes a second expression construct (marked "B") which includes a transactivator of the promoter of the first construct, such as, for example, a T7 RNA polymerase which is preferably fused to nuclear localization signal (marked "NLS"), such that this protein is targeted to the nucleus following its expression. This transactivator is placed under the transcriptional control of a cis-acting regulatory sequence ("CRS") which is specifically regulated by a component or end product of the transduction pathway, such that when the pathway is induced, the transactivator is produced. Thus, in this case, the induction of the pathway leads to the expression of the T7 RNA polymerase and, in turn, to the expression of the insert-GFP fusion. In the cases where a specific insert interacts with pathway components to up regulate or down regulate the pathway, a change in the signal resultant from the reporter gene is detected. It will be appreciated that since the first expression vector includes both the insert and the reporter gene in translational fusion or under the transcriptional control of identical promoters, a feedback loop is formed. Thus, for example, when the expressed insert blocks or interferes with the pathway, the expression of the GFP is down-regulated and a signal is either not initially detected or if detected this signal diminishes or is substantially lower than that of cells which contain inserts which do not interrupt the pathway. In the case of upregulation, a substantial increase in the signal is evident as compared to control cells (e.g., cells in which the first expression construct does not include a library insert). It will be appreciated, that cellular pathways typically are composed of biochemical components which are present in limited amounts, therefore, limited amounts of the library insert expression product are needed to block such a pathway. Thus, interruption of the pathway would typically occur prior to the generation of a detectable signal from the reporter gene product. It will be further appreciated that since it is possible that some cells in which down regulation occurs will still display a detectable signal, fluorescence recovery after photo bleaching can be used to bleach the signal in the cells tested, following which the reappearance of a signal can be monitored. This can be repeated a number of times until cells are detected in which fluorescence is not recoverable.

In a third alternative configuration and as shown in FIG. 3 the expression system includes a single type of expression constructs which form a library. In this case, each expression construct includes the an insert translationally fused to a reporter gene such as GFP. This fusion is under the transcriptional control of a cis-acting regulatory sequence ("CRS") which is specifically regulated by end products of the transduction pathway. Thus, in this case, the induction of the pathway leads to the expression of the fusion (insert-GFP). If a particular insert regulates the pathway, then a negative or positive feedback loop is formed, similar to that described above.

As detailed hereinbelow, the effectiveness of the first alternative configuration of the expression system according to the present invention was examined using restriction fragments of known genes as a library of inserts tested for their regulatory effect on a transduction pathway.

Example 2

IGF-1 receptor signaling

Background

Insulin-like growth factor I (IGF-I) receptor is involved in signaling pathways participating in cell growth, cell development, cell transformation and protection from apoptosis (LeRoith D. et al., Trends Endocrinol. Metab. 1991, Clemmons D R., Growth Regul. 1992, 2:80–87). Similar to other tyrosine kinase growth factor receptors, binding to IGF-I induces receptor autophosphorylation which triggers a signal transduction cellular pathway (Kato H. et al., J. Biol. Chem. 1993, 265:2655–2661, Kato H. et al., Mol. Endocrinol. 1994, Gronborg M. et al., J. Biol. Chem. 1993, 258:23435–23440). The IGF-I activation cascade leads to the activation of several genes, including vascular endothelial growth factor (VEGF) and Hexokinase II (Sebastian S. and Kenkare U W., Biochem Biophys Res Commun, 1997, 235:389–393, Warren R S. Et al., J Biol Chem, 1996, 271:29483–29488, Akagi Y. et al. Cancer Res. 1998, 58:4008–4014). A reporter mammalian cell line suitable for the detection of IGF-1 signaling was constructed. These cells contain the β-galactosidase reporter gene (LacZ) under the transcriptional control of a VEGF or a Hexokinase II promoter, and as such are activated by IGF-1 treatment (demonstrated by FIG. 4).

Following treatment with IGF-1, these cells express the LacZ protein. The presence and level of LacZ expression is determined by using fluorescence flow cytometry which detects and sorts cells in which fluorescence is generated as a result of the activity of the LacZ gene product on a fluorescein di-beta-D-galactopyranoside (FDG-FACS) substrate.

Mammalian cells in which either a green fluorescence protein (GFP) gene (Clontech) was placed under the control of VEGF promoter, a CD4 cell surface marker gene was placed under the control of VEGF promoter or in which a toxin gene (such as *Pseudomonas* toxin A or purtossis toxin) was placed under the control of VEGF promoter were also employed.

Some of the biochemical signaling events induced by the activation of the IGF-1 receptor have been characterized. The IGF-1 receptor is a tyrosine kinase receptor, and as such, IGF-1 binding induces the autophosphorylation of the IGF-1 receptor. Several proteins are activated as a result of this autophosphorylation. For example, insulin receptor-substrate 1 and 2 (IRS1, IRS2) proteins are phosphorylated as a result of the interaction with the activated IGF-1 receptor and as a result promote a mitogenic response. SH2 and SH3 domains of proteins like the proto-oncogene CrkII and CrkL are phosphorylated upon IGF-1 activation (Koval A P, Karas M, Zick Y and LeRoith D. 1998, "Interplay of the proto-oncogene proteins CrL and CrkII in insulin-like growth is factor-1 receptor mediated signal transduction" J Biol Chem 273:14780–14787). A physical interaction was demonstrated between these proteins and a newly identified IRS4. Phosphatidylinositol 3 kinase is activated when IGF-1 receptor is in a phosphorylated state (Bruning J C, Winnay J, Cheatham B, and Kahn C R. 1997, "Differential signaling by insulin receptor substrate 1 (IRS-1) and IRS-2 in IRS-1 deficient cells" Mol Cell Biol 1997 17:1513–1521). EHD 1 interacts with the IGF-1 receptor to mediate its endocytosis and control the Off pathway (Mintz L. et al. Genomics, 1999, 59:66–76 and U.S. patent application Ser. No. 09/026, 898, which is incorporated herein by reference).

Thus, polynucleotides encoding these proteins and other which participate in the IGF signaling pathway are suitable candidates for the construction of DNA libraries. Such libraries can include, for example, random fragments generated as a result of the digestion of these polynucleotide candidates. These random fragments are referred to hereinunder as random lead chimeras (RLC).

Three different RLC libraries have been generated from DNA fragments encoding for human IGF-1 receptor (Gene Bank Accession No. NM000875), IRS-1 (Gene Bank Accession No. S62539) and EHD-1 adapter protein (Gene Bank Accession No. 5803008) (FIGS. 5 and 6a–b).

Materials and Methods preparation of host cells: NIH 3T3 cells expressing the human IGF-1 receptor or the human breast cancer cell line T47D were transfected with the reporter DNA vector containing the reporter gene under the control of the human vascular endothelial growth factor (VEGF) promoter and an antibiotic resistance gene. Introduction of the reporter DNA vectors and the random lead chimera DNA library was performed according to the calcium phosphate transfection method. Cells ($2.5–7 \times 10^5$) were plated in 10 cm dishes 16–24 hours before transfection. Prior to transfection, fresh media was added to the cells. A DNA transfection mixture including 20 mM Hepes pH-7.05, 120 mM $CaCl_2$, 2–10 microgram DNA of interest, 5 mM NaCl, 2 mM KCl, 0.3 mM $Na_2HPO_4$, 1.25 mM sucrose was added to the cells, and the media was replaced the following morning. 48 hours following transfection a portion of the cells was harvested for further manipulation.

DNA Libraries: Human placental mRNA was used to prepare a cDNA clone pool. A sample containing 5 micrograms of total RNA, 2 microliters of oligodT (10 mM) in final volume of 10 microliters was incubated at 80° C. for 10 minutes and immediately chilled on ice. Four microliters of 5× buffer (250 mM Tris-HCl, pH 8.3, 375 mM KCl, 15 mM MgCl$_2$), 2 microliters of 100 mM DTT, and 1 microliter dNTPs (10 mM dTTP, dATP, dCTP and dGTP) were added to the sample to a final volume of 19 microliters. The sample was incubated at 42° C. for 10 minutes following which reverse transcriptase (Superscript II from GibcoBRL) was added (200 Units), and the sample was further incubated at 42° C. for 2 hours.

A 2509 base pair DNA fragment of the human IGF-1 receptor beta chain was PCR amplified from human placenta cDNA using primers 7 and 8 (Table 1). 1783 base pair and 2206 base pair cDNA fragments of the human IRS-1 were PCR amplified using primers 5 and 19 and primers 18 and 29, respectively (Table 1). Both fragments cover the entire human IRS coding sequence.

DNA fragments (FIGS. 7a–b). Digestion with DNase required subsequent Klenow polymerase reaction to fill-in 5' overhangs.

The resultant DNA fragments were each ligated into a pQBI-50 pfA for N terminal cloning and pfC for C terminal cloning (Quantum Biology Inc. USA) in all three open reading frames to generate a separate library for each target gene described above. The ligation reaction was performed in a final volume of 20 microliters and contained 20 nanograms of the vector DNA digested with EcoRV, 10 nanograms of the DNA fragments in 50 mM Tris HCl, 10 mM MgCl$_2$, 10 mM DTT, 1 mM ATP, 5% polyethylene glycol 4000 and 25 micrograms/ml BSA. Each reaction was incubated for 5 hours at 20° C. Each library generated contained approximately 3000 different DNA fragments. Each library was separately introduced into an IGF-1 reporter cell line (described hereinabove) via the calcium phosphate transformation technique as is further described hereinabove. The

TABLE 1

Amplification primers

| No. | Primer Name - position | Primer Sequence | SEQ ID NO. |
|---|---|---|---|
| 3 | 5'F-vegf-Promoter -3400 | 5'-CTGTGCCCTCACTCCCCTGGATCCCTGGG-3' | 1 |
| 4 | 3'R-vegf-Promoter -26 | 5'-GGTTTCGGAGGGCCCGACCGGGGCCGGCCG-3' | 2 |
| 7 | 5'F-IGFIR-Cdna 2746 | 5'-GGGCTGAAGCCCTGGACTCAGTACGC-3 | 3 |
| 8 | 3'R-IGFIR-cDNA 5255 | 5'-GATCCACTGAGGTACAGGAGGCTTGTG-3' | 4 |
| 5 | 5'F-IRS1-cDNA 988 | 5'-CTCTGCTAAGCTTTGGTGGTGGCGGTGG-3' | 5 |
| 6 | 3'R-IRS1-cDNA 4893 | 5'-GGATGCATCGTACCATCTACTGATGAG-3' | 6 |
| 18 | 5'F-I-IRS1 cDNA 2474 | 5'-GTCTCGGGGTGGCAATGGCCACCGCTGC-3' | 7 |
| 19 | 3'R-I-IRS1-cDNA 2762 | 5'-GAGCGGGTGGGCACGAAGGCGGAGTG-3 | 8 |
| 24 | 3'N-R-IRS-1-cDNA 5080 | 5'-GACACGGTGGTGGGCACATCAGCTCAC-3' | 9 |
| 27 | F-In-IRS cDNA 3659 | 5'-GCAGCAGCCCTTGCTGCACCCTCCAGAGCC-3' | 10 |
| 28 | R-In-IRS cDNA 3810 | 5'-CTCTGGGAGCTGGCTGGAGCTGGGATGGAC-3' | 11 |
| 29 | R-end-IRS-cDNA 4680 | 5'-GGTGGAGCTGCTCTCACGGCTGCCCAG-3' | 12 |

Each sample of the PCR reaction included 5 microliters of 10× buffer (200 mM Tris HCl, pH-8.4, 500 mM KCl), 2 microliters of 10 mM dNTP mixture (10 mM of each), 1 mM MgSO$_4$, 0.5 micromolar of each primer, 5 microliters DMSO and 1 microliter Taq DNA polymerase (Platinum Pfx DNA polymerase from GibcoBRL) in a final volume of 50 microliters. The thermocycling reaction included a denaturation step of 95° C. for 5 minutes; followed by 30 cycles, each including: a denaturation step −95° C., of 1 minute, a hybridization step −68° C., 10 seconds, 67° C., 10 seconds, 66° C., 10 seconds, 65° C., 10 seconds, 64° C., 10 seconds, 63° C., 10 seconds, 62° C., 10 seconds and 60° C., 10 seconds; and an elongation step of 68° C., 5 minutes; followed by a final elongation step at 72° C., 10 minutes. Resultant PCR products were analyzed and purified on a TAE agarose gel.

These PCR products were each digested with DpnI, RsaI, HaeIII, BstUI and AluI. thus generating small overlapping final library expression constructs included the various DNA products in fusion to a vector provided fusion protein coding sequence both under the transcriptional control of a CMV or T7 promoters.

Forty eight hours following cell transfection with the random chimera DNA library, cells were treated with the inducer (IGF-1). Cells containing inhibitory sequences are non induced cells and thus did not express the reporter molecule. These cells were sorted and isolated via flow cytometry in the case of GFP reporter cells, or n the case of magnetic beads conujated anti CD4 antibodies. Total RNA was extracted from these cells using a commercially available RNA preparation kit (EZ-RNA kit from Biological Industries, Israel). An RT-PCR reaction was performed, using oligonucleotide primers flanking the multiple cloning site of the library vector (Table 2) in order to isolate DNA inserts thought to be responsible for the inhibitory effect (FIGS. 8a–d).

TABLE 2

Primers flanking the mcs of the vector

| Primer | Sequence | SEQ ID NO: |
|---|---|---|
| pfA1–5'F mcs* | 5'-CGGTAGGCGTGTACGGTGGGAGGTC-3' | 13 |
| pfA1–3'R mcs* | 5'-CTCTCCACTGACAGAGAACTTGTGGCCG-3' | 14 |
| pfC1–5'F mcs** | 5'-CAGCTGCTGGGATTACACATGGCATG-3' | 15 |
| pfC1–3'R mcs** | 5'-GTCGAGGCTGATCAGCGAGCTCTAGC-3' | 16 |

TABLE 2-continued

Primers flanking the mcs of the vector

| Primer | Sequence | SEQ ID NO: |
| --- | --- | --- |

*PCR amplification from the vector without insert, generate a DNA fragment of 318 base pairs.
**PCR amplification from the vector without insert, generate a DNA fragment of 196 base pairs.

Example 3

T Cell Activation Signaling Pathway

Background

Complex T cell interactions with foreign and self-antigens govern and control the immune response. Interaction of an antigen with a T cell receptor initiates intra cellular biochemical events that lead to T cell activation. The hallmark of T cell activation is the transcriptional induction of lymphokines (Crabtree G. R. Science 1989, 243:355–361, van Leeuwen J. E and Samelson L. E. Curr Opin Immunol 1999, 11:242–248, Germain R. N. and Stefanova I, Annu Rev Immunol 1999, 17:467–522). Different T cells induce different sets of lymphokines. For example, interleukin 2 (IL-2) is induced in the case of activated CD4 T cells. The T cell receptor is a protein complex that interacts directly with an antigenic epitope. Several molecules have been identified as being involved in T cell activation (Rab et al. J. Biol. Chem. 1999, 274:21170–21179, Favero J. and Lafont V. 1998, Biochem Pharmacol. 56:1539–1547, Dubey C. and Croft M. 1996, 15:114–125).

Materials and Methods:

Reporter cell line for T cell activation: A T cell line such as, for example, a Jurkat T cell line can be transfected with the appropriate reporter gene driven by the IL-2 promoter and used to monitor T cell activation via the CD3 complex.

DNA Library-T cell signaling: The T cell zeta chain, together with the T cell alpha/beta and gamma/delta heterodimers and CD3 gamma, delta and epsilon chains, form the T cell receptor complex. The zeta chain (Gene Bank Accession No. 4557430) plays an important role in coupling antigen recognition to several intracellular signal transduction pathways. Aberrant or low expression of the zeta chain results in an impaired immune response (Weissman A. M. et al. Proc. Natl. Acad. Sci. 1988, 85:9709–9713). A randomized DNA library is prepared from the human zeta polypeptide chain of the T cell receptor using methods described in Example 2. The library is introduced into a cell line that contains a cell surface protein as a reporter. T cell activation is achieved by treatment with anti-CD3 antibodies combine with ionomycin. The inhibitor sequences are then isolated from cells that do not display the reporter gene, as described in Example 2.

Example 4

Hypoxia Stress

Background

Differential gene expression results from oxygen deficiency in mammalian cells. Oxygen deficiency, termed hypoxia, is a progenitor of a number of processes participating in wound healing, tumor vascularization, diabetic retinopathy, and ischemic heart disease (Folkman J. Nature med. 1995, 27–31, Zachary I. Biochem and Cell Biol. 1998, 30:1169–1174). Several genes are transcriptionally induced during hypoxia, including vascular endothelial growth factor (VEGF), platelet derived growth factor B (PDGF-B), erythropoietin (EPO-I) and others (Kourembanas S. et al., Br. J. Cancer 1990, 62:217–225, Kourembanas S. et al., J. Clin. Invest. 1990, 86:670–764, Goldberg M. A. et al. Science 1988, 242:1412–1414, Shweiki D. et al., Nature 1992, 359:843–845).

Materials and Methods

Reporter cell line for Hypoxia stress: The promoter control elements of hypoxia induced genes share common transcriptional motives. As such, a chimeric transcriptional element including transcriptional elements from several hypoxia induced genes can be a potent activator of a reporter gene in hypoxic cells (Shibata T. et al., Int J Radiat Oncol Biol Phys 1998, 42:913–916). A suitable hypoxia reporter gene such as a cell surface marker can be introduced (as described in Example 2) into endothelial and astrocyte cell lines which respond effectively to hypoxic conditions.

DNA Library-hypoxia stress: Hypoxia inducible factors (HIF) is class of hetero-dimer transcription factors such as VEGF, PDGF-B, Glucose transporter 1 (GLUT 1) and others that mediate hypoxia-induced gene expression. Several cDNAs for HIF proteins were isolated and characterized (Hara S. et al., Biochem. Biophys. Acta. 1999, 1445:237–243, Gu et al., Gene Expression 1998, 7:205–213, Lyer et. al., Genomics 1998, 52:159–165). Small DNA fragments of several HIF sequences are generated and ligated into appropriate vectors as described in Example 2. Since HIF functions in the nucleus, it is crucial that the library includes nuclear known polypeptides so as to target the chimera proteins into the nucleus. An appropriate nuclear targeting signal (NTS) such as that derived from the SV-40 large T antigen is therefore ligated to either the 3' or the 5' of the chimera coding sequence (for review, see Yoneda Y. J. Biochem. 1997, 12:811–817). Once the vectors are introduced into the reporter cell line selection of cells and isolation of desired DNA sequences is performed as described hereinabove.

Example 5

Endocytosis of CD-4 Receptor by HIV-1 Nef Protein

Background

The human and simian immunodeficiency viruses (HIV and SIV) downregulate the cell surface expression of CD4, their primary receptor. In addition, these viruses also downregulate the expression of class 1 histocompatibility complex (MHC-1), a critical mediator of immune recognition. While downregulate the cell surface expression of CD4 is important for viral infectivity, the down regulation of the expression of class 1 histocompatibility complex (MHC-1) most likely promotes immune evasion (Piguet V. et. Al. Immunol Rev. 1999, 168:51–63). Three HIV-1 proteins, Nef, Env and Vpu, contribute to the down regulation of CD4 expression. The Env protein forms a complex with CD4 in the endoplasmic reticulum, thereby retaining the receptor in this cellular compartment. The Nef and Vpu proteins, act to target the CD4 for degradation in the lysosome and the proteosome, respectively. The Nef protein serves as a direct bridge between the CD4 and the cellular endocytic machinery. In addition, the Nef protein also downregulates the surface expression of MHC class I, HLA-A and HLA-B, to avoid detection of HIV infected cells by the cytotoxic T cells (CTL) and the natural killer cells (NK) of the immune system (Cohen G. B. et al., Immunity, 1999, 10:661–671, Kathleen L. et al., Nature, 1998, 391:397–401, Kim Y. H. et al., Virology, 1999, 257:208–219, Piguet V et al., EMBO J, 1998, 17:2472–2481, Foti M. et al., J Cell Biol, 1997, 139:37–47).

Materials and Methods

CD4 endocytosis reporter cell line: The HIV-1 Nef gene can be expressed in a CD4 expressing cell line. In the presence of the Nef protein the CD4 protein is expressed, however, it is not detected on the cell surface. These cells can be monitored for inhibitor molecules by quantitating the levels of cell surface CD4 molecule, using specific fluorescent antibodies.

DNA Library-CD4-Nef system: A DNA library can be generated as described in Example 2 by fragmentation of either the HIV-1 Nef sequences originating from an HXB2 isolate (Gene Bank Accession No. 92105089) or the human CD4 sequences (Gene Bank Accession No. M35160.1). When expressed in a reporter cell line which expresses the HIV-Nef protein and the CD4 surface marker, specific sequences of this library may interfere with the bi-molecular interaction of CD4 and Nef.

Using PCR techniques further described in Example 2, these sequences can be isolated and characterized.

Example 6

Inhibition of TAT Mediated HIV Transcription

Background

The HIV-1 Promoter is located in the 5'LTR and contains a number of regulatory elements important for RNA transcription, including NF-kB, Sp1 and TBP recognition sequences. Transcription of HIV RNA is inefficient at the elongation step and requires the HIV-1 trans-activator of transcription (Tat), which enhance transcription by up to 100 fold. Tat is a small nuclear protein that is essential for virus transcription and replication and is conserved in all lentiviruses. Tat binds to a trans-activator responsive element (TAR) located proximal to the nascent leader of the HIV RNA. In the absence of Tat, the RNA polymerase generally transcribes only a few hundreds nucleotides of the virus transcription unit (Frankel A D, and Young J A, Annu Rev Biochem. 1998, 67:1–25, Ranna T M. and Jeang K T. Arch. Biochem. Biophys. 1999, 365:175–185, Garber M E. and Jones K A. Curr. Opin. Immunol. 1999, 11:460–465). Since the Tat protein is essential for the viral life cycle it is thus a promising candidate for future drug development.

Materials and Methods

Tat reporter cell line: A suitable reporter gene for this system can include the HIV LTR, XhoI-HindIII 350 base pair fragment, containing the TAR region transcriptionally controlling the expression of a LacZ or a CD4 gene. The reporter construct can be stably introduced into mammalian cells, such as the human Jurkat T cells. Cells which contain this construct but which do not express the reporter gene are selected for. These cells are further transfected with a Tat expression plasmid. The Tat plasmid contains a 1500 base pair long SacI-SacI Tat fragment from the HXB II. A 500 base pair region from the SV40 promoter region is used to control the transcription of the Tat fragment. Cells which transcribe the HIV-reporter gene under the control of the Tat gene product are selected using flow cytometry sorting. These cells serve as the reporter cell line for the Tat system.

DNA Library-Tat system: The HIV Tat transcription factor functions in the nucleus. Thus, the chimeras of the Tat system DNA Library also include an SV-40 nuclear localization signal translationaly fused at either the N or C terminal ends of the chimeric insert. The Tat DNA fragments and vector-chimera library are prepared as previously described in Example 2. The Tat DNA Library is transfected into the Tat reporter cell line established as described hereinabove. Cells that lose their ability to activate the reporter gene 48 hours following transfection are selected for by flow cytometry. LacZ activity is assayed via a fluorescent substrate, or in the case of a cell surface marker reporter cell line such as a CD4 expressing cell line, fluorescently tagged anti-CD4 antibodies are added to the culture medium and fluorescence is quantified using flow cytometry.

Although the invention has been described in conjunction with specific embodiments thereof, it is evident that many alternative, modifications and variations will be apparent to those skilled in the art. Accordingly, it is intended to embrace all such alternatives, modifications and variations that fall within the spirit and broad scope of the appended claims. All publications cited herein are incorporated by reference in their entirety.

What is claimed is:

1. An expression library usefull for the detection and isolation of a polypeptide capable of regulating a transduction pathway, the expression library comprising a plurality of expression constructs each including a first coding region encoding one polypeptide of a plurality of polypeptides and a second coding region encoding a reporter molecule, said first and said second coding regions being under the transcriptional control of at least one cis acting regulatory sequence element being regulatable by a trans acting regulator of the transduction pathway, such that when an expression construct of said plurality of expression constructs of said expression library is introduced into a cell, said cell endogenously expressing said trans acting regulator of the transduction pathway, a level of expression of said reporter molecule in said cell within a predetermined range being indicative of regulation of the transduction pathway by a specific polypeptide of said plurality of polypeptides expressed by said cell from said expression construct.

2. The expression library of claim 1, wherein said reporter molecule is an enzyme.

3. The expression library of claim 1, wherein said reporter molecule is a fluorescer.

4. The expression library of claim 3, wherein said fluorescer is selected from the group consisting of green fluorescent protein, blue fluorescent protein, yellow fluorescent protein and cyan fluorescent protein.

5. The expression library of claim 1, wherein said reporter molecule is a eukaryotic cell surface marker.

6. The expression library of claim 1, wherein each of said plurality of expression constructs further includes a selectable marker sequence.

7. The expression library of claim 6, wherein said selectable marker sequence encodes a polypeptide capable of conferring antibiotic resistance to said cell.

8. The expression library of claim 1, wherein said cis acting regulatory sequence element is selected from the group consisting of a promoter and a transcriptional regulatory sequence.

9. The expression library of claim 1, wherein said trans acting regulator of the transduction pathway is selected from the group consisting of a transcriptional regulator and a translational regulator.

10. The expression library of claim 1, wherein each of said plurality of expression constructs further includes a third coding region encoding a known polypeptide, said third coding region being translationaly fused to said first coding region encoding for one of a plurality of polypeptides.

11. The expression library of claim 10, wherein said known polypeptide is capable of targeting said one of a plurality of polypeptides into a subcellular organelle.

12. The expression library of claim 11, wherein said subcellular organelle is a nucleus.

13. The expression library of claim 10, wherein said known polypeptide is capable of targeting said one of a plurality of polypeptides out of said cell.

14. The expression library of claim 1, wherein each of said plurality of polypeptides is of a specific size selected from a size range of approximately 5 amino acids to approximately 1000 amino acids.

15. The expression library of claim 14, wherein each of said plurality of polypeptides is of a specific size selected from a size range of approximately 10 amino acids to approximately 100 amino acids.

16. The expression library of claim 15, wherein said portion of a polynucleotide sequence represented in a genome is a digest product of a genome.

17. The expression library of claim 15, wherein said portion of a polynucleotide sequence represented in a genome is a PCR product.

18. The expression library of claim 1, wherein said polypeptide is selected from the group consisting of a characterized polypeptide, a portion of a characterized polypeptide, a combinatorial polypeptide and a polypeptide chimera.

19. The expression library of claim 1, wherein said cell is a eukaryotic cell.

20. A method of detecting a polypeptide capable of regulating a transduction pathway, the method comprising the step of:

(a) introducing into cells endogenously expressing a trans acting regulator of the transduction pathway an expression library, said expression library including a plurality of expression constructs each including a first coding region encoding one polypeptide of a plurality of polypeptides and a second coding region encoding a reporter molecule, said first and said second coding regions being under the transcriptional control of at least one cis acting regulatory sequence element being regulatable by said trans acting regulator of the transduction pathway, (b) monitoring the level of expression of said reporter molecule in said cells, a level of expression within a predetermined range being indicative of regulation of the transduction pathway by a polypeptide of said plurality of polypeptides; and (c) isolating said first coding region from a cell of said cells in which the level of expression of said reporter molecule is within said predetermined range.

21. The method of claim 20, wherein said reporter molecule is an enzyme.

22. The method of claim 20, wherein said reporter molecule is a fluorescer.

23. The method of claim 22, wherein said fluorescer is selected from the group consisting of green fluorescent protein, blue fluorescent protein, yellow fluorescent protein and cyan fluorescent protein.

24. The method of claim 20, wherein said reporter molecule is a eukaryotic cell surface marker.

25. The method of claim 20, wherein step (a) is effected via a transformation method selected from the group consisting of biolistic bombardment, direct DNA uptake, virus mediated transformation and calcium phosphate transformation.

26. The method of claim 20, wherein said step of monitoring a level of expression of said reporter molecule in said cells is effected via an automated cell sorter.

27. The method of claim 20, wherein said step of isolating said first coding region is effected via a PCR reaction using oligonucleotide primers flanking said first coding region.

28. The method of claim 20, wherein said cis acting regulatory sequence element is selected from the group consisting of a promoter and a transcriptional regulatory sequence.

29. The method of claim 20, wherein said trans acting regulator of the transduction pathway is selected from the group consisting of a transcriptional regulator and a translational regulator.

30. The method of claim 20, wherein each of said plurality of expression constructs further includes a third coding region encoding a known polypeptide, said third coding region being translationaly fused to said first coding region encoding for one of a plurality of polypeptides.

31. The method of claim 30, wherein said known polypeptide is capable of targeting said one of a plurality of polypeptides into a subcellular organelle.

32. The method of claim 31, wherein said subcellular organelle is a nucleus.

33. The method of claim 30, wherein said known polypeptide is capable of targeting said one of a plurality of polypeptides out of said cell.

34. The method of claim 20, wherein each of said plurality of polypeptides is of a specific size selected from a size range of approximately 5 amino acids to approximately 1000 amino acids.

35. The method of claim 34, wherein each of said plurality of polypeptides is of a specific size selected from a size range of approximately 10 amino acids to approximately 100 amino acids.

36. The method of claim 35, wherein said portion of a polynucleotide sequence represented in a genome is a digest product of a genome.

37. The method of claim 35, wherein said portion of a polynucleotide sequence represented in a genome is a PCR product.

38. The method of claim 20, wherein said polypeptide is selected from the group consisting of a characterized polypeptide, a portion of a characterized polypeptide, a combinatorial polypeptide and a polypeptide chimera.

39. The method of claim 20, wherein said cell is a eukaryotic cell.

* * * * *